US009434661B2

(12) United States Patent
Ou et al.

(10) Patent No.: US 9,434,661 B2
(45) Date of Patent: Sep. 6, 2016

(54) PHENOL REMOVAL IN PARAXYLENE RECOVERY PROCESS

(71) Applicant: ExxonMobil Chemical Patents Inc., Baytown, TX (US)

(72) Inventors: John Di-Yi Ou, Houston, TX (US); Glenn A. Heeter, The Woodlands, TX (US); Shifang L. Luo, Annandale, NJ (US); Indulis J. Eilands, League City, TX (US); Jeevan S. Abichandani, Houston, TX (US); Allen S. Gawlik, Houston, TX (US); Mark W. Nash, Baytown, TX (US); Terrance C. Osby, Manvel, TX (US); Robert G. Tinger, Friendswood, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/642,000

(22) Filed: Mar. 9, 2015

(65) Prior Publication Data

US 2015/0299070 A1    Oct. 22, 2015

Related U.S. Application Data

(63) Continuation of application No. 13/875,402, filed on May 2, 2013, now Pat. No. 9,012,711.

(60) Provisional application No. 61/681,501, filed on Aug. 9, 2012, provisional application No. 61/653,698, filed on May 31, 2012.

(51) Int. Cl.
*B01J 19/24* (2006.01)
*C07C 2/86* (2006.01)
*C07C 7/13* (2006.01)

(52) U.S. Cl.
CPC ............... *C07C 2/864* (2013.01); *B01J 19/24* (2013.01); *B01J 19/245* (2013.01); *C07C 2/865* (2013.01); *C07C 7/13* (2013.01); *B01J 2219/24* (2013.01); *C07C 2529/85* (2013.01)

(58) Field of Classification Search
None
See application file for complete search history.

(56) References Cited

U.S. PATENT DOCUMENTS

| 2,943,105 | A | 6/1960 | Caruthers |
| 3,017,426 | A | 1/1962 | Ruffing et al. |
| 3,409,691 | A | 11/1968 | Small |
| 3,751,507 | A | 8/1973 | Walker |
| 4,064,042 | A | 12/1977 | Kunin |
| 4,404,118 | A | 9/1983 | Herskovits |

(Continued)

FOREIGN PATENT DOCUMENTS

| CN | 1253937 | 5/2000 |
| EP | 1 186 343 | 3/2002 |

(Continued)

OTHER PUBLICATIONS

Chemicals Product Data, Selexsorb CDX, Selective Adsorbent, Mar. 1993, Alcoa Industrial Chemicals Division SEP 958.

*Primary Examiner* — Tam M Nguyen (57) ABSTRACT

The invention is directed to purification of an aromatic hydrocarbon stream including selective removal of phenol from a process stream comprising aromatic hydrocarbon mixtures, especially aromatic hydrocarbon mixtures that contain higher-than-equilibrium paraxylene, by contact with suitable adsorbents, to provide a product stream having lower concentration of phenol than said process stream.

17 Claims, 4 Drawing Sheets

(56) References Cited

U.S. PATENT DOCUMENTS

| | | |
|---|---|---|
| 4,453,029 A | 6/1984 | Dessau |
| 4,469,805 A | 9/1984 | Kofke, Jr. et al. |
| 5,218,132 A | 6/1993 | Mobbs et al. |
| 6,281,406 B1 | 8/2001 | Cain |
| 6,423,879 B1 | 7/2002 | Brown et al. |
| 6,504,072 B1 | 1/2003 | Brown et al. |
| 6,555,611 B2 | 4/2003 | Tachifuji et al. |
| 7,022,161 B2 | 4/2006 | Nedez |
| 8,252,967 B2 | 8/2012 | Hagemeister et al. |
| 2002/0082462 A1 | 6/2002 | Ferraro et al. |
| 2011/0009682 A1 | 1/2011 | Matsushita et al. |
| 2011/0201863 A1 | 8/2011 | Matsushita et al. |
| 2012/0316375 A1 | 12/2012 | Zheng et al. |
| 2013/0324779 A1* | 12/2013 | Heeter ............... C07C 7/13 585/466 |
| 2013/0324780 A1 | 12/2013 | Ou et al. |
| 2014/0088277 A1 | 3/2014 | Stewart et al. |
| 2016/0115094 A1* | 4/2016 | Dakka ............... C07C 2/865 562/414 |

FOREIGN PATENT DOCUMENTS

| | | |
|---|---|---|
| JP | 56039025 | 4/1981 |
| JP | 7215901 | 8/1994 |
| WO | WO 99/38823 | 8/1999 |
| WO | WO 00/35836 | 6/2000 |

\* cited by examiner

PHENOL REMOVAL IN PARAXYLENE RECOVERY PROCESS

CROSS REFERENCE TO RELATED APPLICATIONS

This application is a continuation of and claims priority to and the benefit of U.S. patent application Ser. No. 13/875,402, filed May 2, 2013, U.S. Provisional Application No. 61/681,501, filed Aug. 9, 2012, and U.S. Provisional Application No. 61/653,698, filed May 31, 2012, the disclosures of which are incorporated herein by reference in their entirety.

FIELD OF THE INVENTION

The invention relates to removal of phenol from aromatic hydrocarbon mixtures, and more particularly, removal of phenol from aromatic hydrocarbon mixtures containing higher than equilibrium paraxylene concentrations, and to purification of process streams in the production of paraxylene by alkylation of benzene and/or toluene with methanol and/or demethylether (DME).

BACKGROUND OF THE INVENTION

Of the aromatic C8 isomers, including the three xylene isomers and ethylbenzene, paraxylene is of particularly high value since paraxylene is useful in the manufacture of synthetic fibers and resins. Refinery and chemical plant streams containing the aromatic C8 isomers typically contain, at thermodynamic equilibrium, only about 22-24 wt % paraxylene, based on the weight of the xylene isomers in the stream. Separation of paraxylene from the other C8 isomers requires superfractionation and/or multistage refrigeration steps and/or adsorptive separation, all of which are energy intensive. There is a need to provide processes for producing paraxylene in more efficient ways, such as in higher selectivity than can be obtained from refinery and chemical plant streams.

One known method for producing paraxylene selectively involves the alkylation of toluene and/or benzene with methanol and/or dimethylether (DME) over a solid acid catalyst. Selectivities to paraxylene in excess of 90 wt % (based on total $C_8$ aromatic product) have been reported by reacting toluene with methanol in the presence of a catalyst comprising a porous crystalline material, preferably a medium-pore zeolite and particularly ZSM-5, having a Diffusion Parameter for 2,2 dimethylbutane of about 0.1-15 $sec^{-1}$ when measured at a temperature of 120° C. and a 2,2 dimethylbutane pressure of 60 torr (8 kPa). See U.S. Pat. Nos. 6,423,879 and 6,504,072.

WO 99/38823 reported a reactive distillation process comprising the contact of toluene with a methylating agent in the presence of a zeolite in a reaction/distillation column produces, as a side product, DME, which can be recycled (with unreacted methanol) to extinction in the process. The process operates at no greater than 320° C.

It has recently been discovered that the alkylation of benzene and/or toluene with methanol can also result in the production of a variety of oxygenates, in addition to DME, but also other oxygenate by-products. See for instance U.S. patent application Ser. No. 13/487,651. According to the invention described in Ser. No. 13/487,651, the concentration of phenolic impurities in a xylene stream produced by alkylation of benzene and/or toluene with methanol can be reduced to trace levels, e.g., below 0.1 ppmw, by one or more washing treatments with an aqueous solution of a base. The resultant treated xylene stream, if necessary after water washing to remove any phenate-containing solution, can then be recycled to the xylene splitter to generate additional para-xylene or can be used as a solvent. This discovery was surprising, as phenol is not present in reformate streams, which is the traditional source of xylene streams.

It has also recently been discovered that xylenes produced by alkylating toluene and/or benzene with an alkylating agent comprising methanol and/or DME over a solid acid catalyst contain small quantities of styrene, which, if not removed, could cause operability problems for downstream paraxylene recovery processes, or even further, in processes using paraxylene, such as the production of terephthalic acid, and derivatives thereof, including polyester fibers, films, and the like. See co-filed U.S. patent application Ser. No. 13/875,373.

Several characteristics of the xylene produced by alkylation of benzene and/or toluene make styrene removal challenging. The desired product, paraxylene, is present at higher-than-equilibrium concentration. The material used to remove phenol must therefore show minimal xylenes isomerization activity. The catalyst must also minimize formation of benzene, which also can have detrimental effects on downstream processing. Furthermore, as discussed above, the product may also contain styrene as well as other olefinic compounds that may enter the alkylation reaction system via the feedstream of toluene, such as catalytic reforming units, which are a source of toluene for the aforementioned alkylation reaction. These and other problems make the treatment of the product stream from the alkylation of benzene and/or toluene in the presence of an acid catalyst difficult.

It has long been known that certain substances have selective adsorption characteristics useful in resolving mixtures into component parts. See, for instance, U.S. Pat. No. 4,453,029, which teaches the use of certain zeolites in selective separation of certain mono- and para-disubstituted benzene ring compounds and mono-substituted pyridine ring compounds in admixture with aromatic compounds selected from the group consisting of ortho-disubstituted, meta-disubstituted and more highly substituted benzene ring compounds and poly-substituted pyridine ring compounds.

Other relevant prior art includes U.S. Pat. No. 6,555,611, teaching an absorbent for aromatic hydroxyl compound comprising composite metal oxide solid solution particles or hydrotalcite-like composite metal hydroxide particles; JP 56039025A, teaching removal of phenols from organic matter by contact with a polyvinyl pyridine resin; CN 1253937A, teaching using silica gel to remove phenol-like compounds from styrene monomers; U.S. Pat. No. 3,409,691, teaching removal of phenol by the use of macroporous ion exchange resin; U.S. Pat. No. 4,064,042, teaching separating an organic component such as phenol from blood by contact with a macroporous synthetic polymer; U.S. Pat. No. 5,218,132, teaching removal of aromatic impurities such as phenol by contact with a material including a smectite mineral; and JP 7215901A, teaching contact of a phenol-containing non-aqueous solvent with an acrylic weak basic ion exchange resin. See also U.S. Pat. Nos. 8,252,967; 7,022,161; 4,469,805; 4,404,118; 2,943,105; U.S. Patent Publication 2012-0316375 and U.S. patent application Ser. No. 13/618,211.

The present inventors have surprisingly discovered a method for selective removal of phenol from a process stream comprising hydrocarbon mixtures, especially hydrocarbon mixtures that contain higher-than-equilibrium paraxylene.

SUMMARY OF THE INVENTION

The invention is directed to purification of an aromatic hydrocarbon stream including selective removal of phenol from a process stream, said process comprising the contact of benzene and/or toluene with an alkylating agent in the presence of a suitable alkylation catalyst under appropriate conditions to selectively produce paraxylene, said selective removal of phenol comprising the contact of said process stream with a suitable material under conditions effective to provide a product stream from said process, said product stream having a lower concentration of phenol than said process stream, preferably less than 10 ppm wt, more preferably less than 1.0 ppm wt. The alkylating agent is preferably selected from methanol, dimethylether (DME) and mixtures thereof.

The process is also directed to a process for the production of paraxylene selectively by: (i) reacting of toluene and/or benzene with an alkylating agent, preferably methanol and/or dimethylether (DME), in the presence of a suitable alkylation catalyst under appropriate conditions to selectively produce a process stream comprising paraxylene in higher than equilibrium amounts; and (ii) contact of said process stream comprising paraxylene in higher than equilibrium amounts with a suitable material to remove phenol and provide a product stream having lower concentration of phenol than said process stream.

Suitable materials used to remove phenol from the process stream include alumina, silica, molecular sieves, zeolites, basic organic resins, and mixtures thereof.

In embodiments, said process stream may be subjected to additional process steps such as fractionation or adsorptive separations to remove species other than phenol. In embodiments, the process stream treated to provide a lower concentration of phenol may be the feedstream to the alkylation process, such as the toluene stream from a catalytic reforming unit, or a stream comprising xylenes downstream of the alkylation reactor, such as upstream of a fractionator used to separate unreacted toluene (e.g., "detol fractionator") and/or methanol from the alkylation reactor product xylene stream, the bottoms and/or overhead product from said detol fractionator, a xylenes splitter, such as utilized to separate heavy aromatics (C9+ aromatic hydrocarbons) from the xylene product, upstream or downstream from a paraxylene recovery unit (e.g., adsorptive separation, such as a Parex™ adsorptive separation unit or Eluxyl™ adsorptive separation unit, or a crystallization apparatus), upstream or downstream of an isomerization unit (which may be liquid phase or vapor phase), and the like. The process stream may also comprise an imported process stream or any other type of stream which has picked up oxygenate impurities, particularly phenol, such as from a previous cargo.

In embodiments, the process also comprises regeneration of said material, preferably by heating under continuous flow of wet inert gas, such as at greater than or equal to 100° C. in the presence of a continuous flow of $N_2$ small amounts of steam, such as amounts measured in ppm-range (e.g., 1-1000 ppm or 10-600 ppm, or 100-500 ppm) or by competitive adsorption using a polar adsorbent, such as alcohols, to displace the adsorbed phenol, and combinations thereof. In embodiments said regeneration may also be selected from one or more of: (1) purge with mixture(s) of $N_2$ or other inert gas and at least one organic solvent such as aromatics, alcohols, ketones, and the like or at least one inorganic solvent such as water, $CO_2$, $CS_2$, etc., at temperatures such as >20° C.; (2) purge with an organic solvent such as aromatics, alcohols, ketones, etc., or an inorganic solvent such as water, $CO_2$, $CS_2$, and the like in either liquid phase or vapor phase at temperatures such as >20° C. followed by a $N_2$ (or other inert gas) purge at temperatures such as >100° C.; (3) purge with mixture(s) of at least one organic solvent and at least one inorganic solvent at, for instance, >25° C., followed by a $N_2$ purge at temperatures such as >150° C.; and (4) purge with air, mixture of oxygen and nitrogen, steam, or mixtures thereof at, by way of example, temperatures >150° C.

By "selectively produce paraxylene" and similar phrases is meant the production of xylenes wherein paraxylene is present in amounts greater than is present in an equilibrium mixture of C8 aromatic isomers, and by "equilibrium mixture" or "equilibrium amounts" with reference to the concentration of paraxylene in a mixture of C8 aromatic isomers is meant generally about 22-24 wt %. Preferably, the alkylation reaction produces a product stream having at least 70 wt %, such as 75 wt %, 80 wt %, 85 wt %, 90 wt %, (all wt % herein based on the total amount of C8 aromatic isomers unless otherwise specified), to about 99 wt % or even higher, particularly in the ranges of 70-90 wt %, 75-88 wt %, 80-95 wt %, 82-88 wt %, or in the range of from any lower wt % disclosed to any higher wt % disclosed.

In embodiments the amount of phenol present after said contact with a catalyst suitable for selective removal of phenol is less than 20 ppm wt, more preferably less than 10 ppm wt, still more preferably less than 1 ppm wt, based on the total amount of aromatic hydrocarbon.

By "selective removal of phenol" means that the amount of phenol removed in the phenol-removal contacting step is, in embodiments, equal to or greater than the amount of phenol produced in the alkylation reaction, or so that the final product after the styrene removal step is less than 20 ppm wt, or less than 10 ppm wt, or less than 1 ppm wt., and/or greater than the amount of benzene produced in said step, and/or greater than the amount of paraxylene isomerization that occurs in said phenol removal step.

In embodiments said process stream may be subjected to additional process steps such as fractionation, adsorptive separations, crystallization, membrane separation, and the like, to remove species other than phenol.

In embodiments, said contact may be in the presence of hydrogen or it can be in the absence of hydrogen.

It is an object of the invention to provide a continuous, semi-continuous, or batch process of purifying xylene feedstream of phenol and phenolic-like impurities by contact with a material, such as an adsorbent, that can be regenerated.

It is another object of the invention to provide an apparatus adapted for the process of the invention.

These and other objects, features, and advantages will become apparent as reference is made to the following detailed description, preferred embodiments, examples, and appended claims.

DETAILED DESCRIPTION

According to the invention, there is a process for purification of an aromatic hydrocarbon stream by selective adsorption. By selective adsorption is meant that phenol is removed in amounts higher than the amount of xylenes, particularly paraxylene, such as by contact of said stream with a material selected from alumina, silica, molecular sieves, zeolites, basic organic resins, and mixtures thereof. In a particularly preferred embodiment it comprises removal of phenol by selective adsorption of phenol with a suitable adsorbent from a process stream comprising higher than equilibrium amounts of paraxylene and also oxygenate contaminants, wherein said higher than equilibrium amounts of paraxylene and said oxygenate contaminants are produced by the reaction of an alkylating agent selected from methanol, DME, and mixtures thereof, with toluene and/or benzene in the presence of a suitable catalyst under appropriate conditions.

In embodiments, the process also comprises regeneration of said material, preferably by heating under continuous flow of wet inert gas, such as at greater than or equal to 100° C. in the presence of a continuous flow of $N_2$ and small amounts of steam, such as amounts measured in ppm-range (e.g., 1-100 ppm or 1-25 ppm, or 1-10 ppm) or by competitive adsorption using a polar adsorbent, such as alcohols, to displace the adsorbed phenol, and combinations thereof. In embodiments said regeneration may also be selected from one or more of: (1) purge with mixture(s) of $N_2$ and at least one organic solvent such as aromatics, alcohols, ketones, and the like or at least one inorganic solvent such as water, $CO_2$, $CS_2$, etc., at temperatures such as >20° C.; (2) purge with an organic solvent such as aromatics, alcohols, ketones, etc., or an inorganic solvent such as water, $CO_2$, $CS_2$, and the like in either liquid phase or vapor phase at temperatures such as >20° C. followed by a $N_2$ purge at temperatures such as >100° C.; (3) purge with mixture(s) of at least one organic solvent and at least one inorganic solvent at, for instance, >25° C., followed by a $N_2$ purge at temperatures such as >150° C.; and (4) purge with air, mixture of oxygen and nitrogen, low amount of steam (again, at ppm levels), or mixture thereof at, by way of example, temperatures >150° C.

Successful regeneration in the presence of low levels of steam is surprising as heretofore it would be thought that such materials would convert essentially to a cement-like material when contacted with steam.

In embodiments the preferred adsorbents are selected from alumina, silica, molecular sieves and/or zeolites, basic organic resins, and mixtures thereof, and in still a more preferred embodiment are Amberlyst™ A260H and/or Selexorb™ CDX. There terms "molecular sieve" and "zeolites" are used synonymously herein.

In preferred embodiments, there is also a step of recovery of paraxylene by crystallization, adsorption, and the like. More preferably, after the selective adsorption of phenol with a suitable adsorbent, to provide a phenol-depleted stream comprising xylenes, there is the step of selective removal of paraxylene to provide a paraxylene-enriched aromatic hydrocarbon stream and a paraxylene-depleted aromatic hydrocarbon stream. Particularly preferred methods include use of a Parex™ unit or Eluxyl™ unit.

A typical composition of xylenes produced from the reaction of toluene with methanol in the presence of a solid acid catalyst is shown in Table 1.

TABLE 1

| Compound | wt % |
| --- | --- |
| Toluene | 0.0950 |
| Styrene | 0.0648 |
| mixed xylenes | 94.56 |

TABLE 1-continued

| Compound | wt % |
| --- | --- |
| Ethylbenzene | 0.47 |
| C9 aromatics | 4.7574 |
| Phenol | 0.0014 |
| other oxygenates | >0.05 |

Representative species found in the product include 1,2, 4-trimethylbenzene, 1-methyl-4-ethylbenzene, n-nonane, naphthalene, 1,4-dimethyl-2-ethylbenzene, biphenyl, anthracene, C16 aromatic alkylates, benzoic acid, 4-methylbenzoic acid, o-cresol, 2,4-dimethylphenol, and the like.

The presence of phenol and phenolic species in a stream of xylenes in processes downstream of their production, e.g., the preparation of terephthalic acid and derivatives thereof, can be a problem, and depending on the final product, need to be present in very small to vanishing (no trace) amounts.

The invention may still better be understood by reference to the following specific examples, which are intended to illustrate, but not limit, the scope of this invention. One of skill in the art in possession of the present disclosure will appreciate that the invention may be practiced other than as specifically illustrated.

Examples 1-14

Phenol Adsorption with Selexorb™ CDX at 40° C. and 20° C.

Pre-weighted and pre-dried adsorbent Selexorb CDX was added to mixed xylene solutions that contained phenol of various concentrations. The mixtures were kept at 40° C. or 20° C. for 96 hours. Phenol concentration of the hydrocarbon solution was then determined by GC chromatography. Results, shown in Table 1, demonstrated Selexorb CDX's capability in selective adsorption of phenol in hydrocarbons.

Examples 15-20

Regeneration of Selexorb™ CDX Adsorbent

Pre-weighted and pre-dried adsorbent Selexorb CDX (~2.30 grams) was added to mixed xylene solutions (~8.70 grams) that contained phenol of various concentrations. The mixture was kept at 40° C. for 96 hours. Afterwards, the spent adsorbents were recovered by filtration and regenerated under a continuous $N_2$ flow at temperatures of 150, 200, and 280° C. for 72 hours, respectively. The regenerated adsorbents were then used in the second cycle of phenol adsorption experiment. This adsorption-regeneration cycle was repeated.

Table 2 lists phenol concentrations in hydrocarbons after each adsorption cycle. A comparison of this data from these consecutive cycles suggested that regeneration under a continuous purge of inert gas such as $N_2$ recovered the majority of Selexorb CDX's phenol adsorption capacity.

Example 21

Phenol Adsorption with Selexorb™ CDX in Presence of Styrene

The above experiment was repeated with Selexorb CDX with a hydrocarbon solution that contained phenol and styrene. Results, shown in Table 3, demonstrated Selexorb CDX's selectivity towards phenol when a hydrocarbon solution contains both styrene and phenol.

Example 22

Phenol Adsorption with Selexorb™ CDX in Presence of Styrene—Regeneration

The spent absorbent from Experiment 21 was recovered and regenerated under a continuous $N_2$ flow at 280° C. for 72 hours. The regenerated adsorbent was then used in the $2^{nd}$ cycle of the phenol adsorption experiment. Results, shown in Table 3, indicated that Selexorb CDX retained its selectivity towards phenol after the regeneration.

Examples 23-26

Phenol Adsorption with Amberlyst™ A260H at 20° C. and 40° C.

Experiments 1-14 were repeated with Amberlyst A260H as the adsorbent at 20° C. and 40° C., respectively. Results, shown in Table 4, indicated Amberlyst A260H's ability to selectively adsorb phenol in hydrocarbons.

TABLE 1

Adsorption of Phenol in Hydrocarbon with Selexorb ™ CDX

| | | Adsorbent | | Hydrocarbon Solutions | |
| | | | | Phenol Concentration, ppm | |
| Experiment | Temperature, ° C. | Name | Weight (g) | Weight (g) | Before Adsorption | After Adsorption |
|---|---|---|---|---|---|---|
| 1 | 40 | Selexorb CDX | 2.31 | 8.71 | 1,122 | 0.42 |
| 2 | 40 | Selexorb CDX | 2.31 | 8.71 | 2,129 | 1.65 |
| 3 | 40 | Selexorb CDX | 2.34 | 8.72 | 3,168 | 1.84 |
| 4 | 40 | Selexorb CDX | 2.30 | 8.75 | 4,149 | 2.67 |
| 5 | 40 | Selexorb CDX | 2.30 | 8.72 | 6,124 | 5.44 |
| 6 | 40 | Selexorb CDX | 2.29 | 8.68 | 8,010 | 11.43 |
| 7 | 40 | Selexorb CDX | 2.33 | 8.75 | 11,191 | 42.91 |
| 8 | 20 | Selexorb CDX | 2.33 | 8.71 | 1,122 | 0.00 |
| 9 | 20 | Selexorb CDX | 2.30 | 8.75 | 4,149 | 1.52 |
| 10 | 20 | Selexorb CDX | 2.32 | 8.70 | 10,258 | 4.38 |
| 11 | 20 | Selexorb CDX | 2.26 | 8.56 | 11,191 | 7.73 |
| 12 | 20 | Selexorb CDX | 2.30 | 8.71 | 14,380 | 15.33 |
| 13 | 20 | Selexorb CDX | 2.31 | 8.70 | 17,549 | 39.85 |
| 14 | 40 | Selexorb CDX | 2.50 | 8.71 | 2,166 | 7.04 |

TABLE 2

Adsorption of Phenol in Hydrocarbon with Selexorb-Adsorbent Regeneration

| | Experiment | | | | | |
|---|---|---|---|---|---|---|
| | 15 | 16 | 17 | 18 | 19 | 20 |
| | Regen Temp (° C.) | | | | | |
| | 150 | 150 | 200 | 200 | 280 | 280 |
| | Initial Phenol Conc (wt %) | | | | | |
| Adsorption Cycle | 0.2 | 0.4 | 0.2 | 0.4 | 0.2 | 0.4 |
| | Phenol Concentration after Adsorption (ppm) | | | | | |
| 1 | 4.35 | 6.35 | 11.43 | 5.44 | 2.67 | 4.29 |
| 2 | 17.80 | 52.25 | 511.77 | 250.77 | 37.84 | 25.48 |
| 3 | 8.04 | 22.15 | 19.49 | 27.57 | 1.29 | 6.51 |
| 4 | 3.12 | 23.39 | 1.73 | 18.63 | 0.35 | 4.73 |
| 5 | 17.80 | 83.00 | 4.30 | 12.40 | 1.50 | 6.70 |

TABLE 2-continued

Adsorption of Phenol in Hydrocarbon with Selexorb-Adsorbent Regeneration

| | Experiment | | | | | |
|---|---|---|---|---|---|---|
| | 15 | 16 | 17 | 18 | 19 | 20 |
| | Regen Temp (° C.) | | | | | |
| | 150 | 150 | 200 | 200 | 280 | 280 |
| | Initial Phenol Conc (wt %) | | | | | |
| Adsorption Cycle | 0.2 | 0.4 | 0.2 | 0.4 | 0.2 | 0.4 |
| | Phenol Concentration after Adsorption (ppm) | | | | | |
| 6 | 24.80 | 69.36 | 10.13 | 41.93 | 4.51 | 17.90 |
| 7 | 155.87 | 565.45 | 79.99 | 223.65 | 26.43 | 134.11 |
| 8 | 156.19 | 645.16 | 316.80 | 32.12 | 6.23 | 23.76 |
| 9 | 767.24 | 1830.25 | 113.12 | 291.22 | 31.72 | 233.53 |
| 10 | 370.98 | 1128.19 | 35.10 | 134.06 | 17.62 | 82.21 |
| 11 | 595.98 | 1324.23 | 71.42 | 181.17 | 28.78 | 122.40 |
| 12 | | | 57.88 | | 26.10 | 123.70 |
| 13 | | | 59.59 | | 32.64 | 103.03 |
| 14 | | | 86.85 | | 72.30 | 170.87 |

TABLE 3

Adsorption of Phenol in Styrene-containing Hydrocarbons with Selexorb ™ CDX

| Experiment | 21 | 22 |
|---|---|---|
| Adsorption Cycle | Fresh | 2 |
| Regen Temp (deg C.) | | 280 |
| Initial Phenol Conc (wt %) | 0.22 | 0.22 |
| Final Phenol Concentration, ppm | 4.12 | 7.04 |
| Initial Styrene Conc (ppm) | 19.50 | 19.53 |
| Final Styrene Conc (ppm) | 19.70 | 19.32 |

TABLE 4

Adsorption of Phenol in Hydrocarbons with Amberlyst ™ A26OH

| | | Adsorbent | | | Hydrocarbon Solutions | |
| | | | | | Phenol Concentration, ppm | |
| Experiment | Temperature, ° C. | Name | Weight (g) | Weight (g) | Before Adsorption | After Adsorption |
|---|---|---|---|---|---|---|
| 23 | 40 | Amberlyst A26OH | 2.32 | 8.70 | 1,984 | 96 |
| 24 | 40 | Amberlyst A26OH | 2.30 | 8.73 | 3,926 | 148 |
| 25 | 40 | Amberlyst A26OH | 2.30 | 8.66 | 6,135 | 815 |
| 26 | 40 | Amberlyst A26OH | 2.30 | 8.71 | 8,242 | 898 |
| 27 | 40 | Amberlyst A26OH | 2.31 | 8.71 | 10,258 | 1,150 |
| 28 | 20 | Amberlyst A26OH | 2.30 | 8.72 | 1,984 | 65 |
| 29 | 20 | Amberlyst A26OH | 2.31 | 8.76 | 3,926 | 197 |
| 30 | 20 | Amberlyst A26OH | 2.33 | 8.76 | 6,124 | 366 |
| 31 | 20 | Amberlyst A26OH | 2.31 | 8.69 | 8,010 | 737 |
| 32 | 20 | Amberlyst A26OH | 2.30 | 8.71 | 10,258 | 801 |

The following additional experiments are also intended to be representative and not limiting.

Example 27

Adsorption on Fresh Selexsorb CDX at 5 WHSV

A fixed bed of fresh Selexsorb CDX alumina obtained from the BASF Company was mixed with quartz sand in a ⅜" stainless reactor. The mixture was dried at 280° C. under continuous $N_2$ flow for 14-20 hrs. Afterwards, a mixed xylene solution containing 6.5 ppm phenol was fed into the reactor at 40° C. and 5 WHSV. Samples of outlet liquids were collected at regular intervals and analyzed for the phenol concentration. Results are plotted in FIG. 3.

Example 28

Adsorption on the 1st Cycle N2-Regenerated Selexsorb CDX at 5 WHSV

Figure 3:
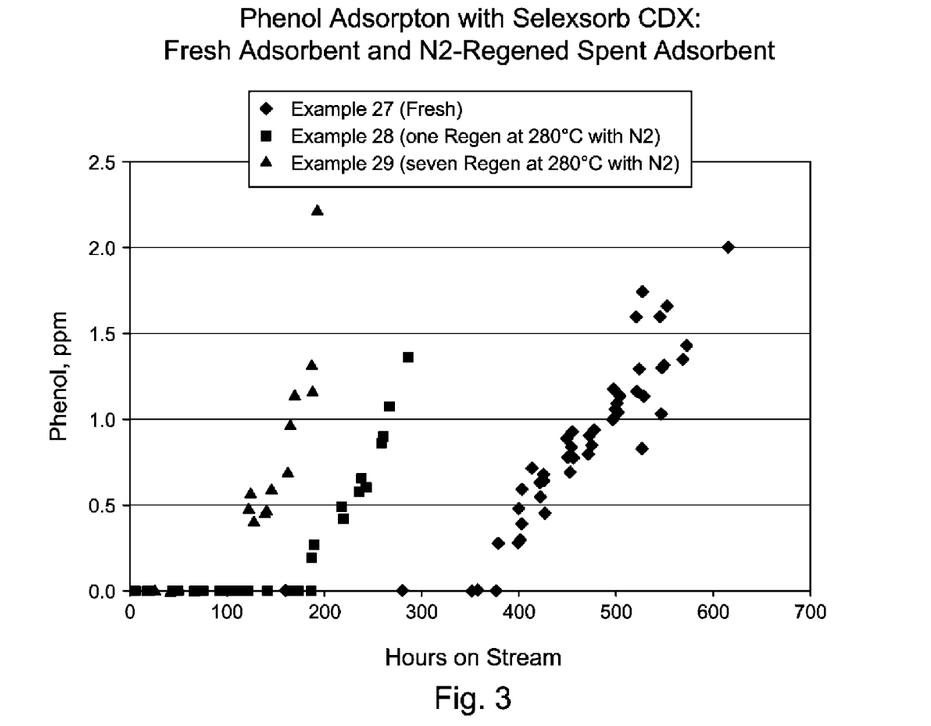
FIGS. 3-4 show experimental results on one or more embodiments of the invention.

The spent adsorbent from Example 27 was regenerated at 280° C. under continuous N2 flow. After regeneration, the adsorbent was tested for phenol adsorption, following the same procedure as that of Example 27. Results are shown in FIG. 3.

Example 29

Adsorption on the 7th Cycle N2-Regenerated Selexsorb CDX at 5 WHSV

A spent adsorbent Selexsorb CDX, regenerated with N2 at 80° C. for seven times, was used in phenol adsorption, following the same procedure as that of Example 27. Results are shown in FIG. 3.

Example 30

Adsorption on Fresh Selexsorb CDX at 20 WHSV

A fixed bed of fresh Selexsorb CDX and quartz sand in a ⅜" stainless reactor was dried at 280° C. under a continuous N2 flow for 14-20 hrs. Afterwards, a mixed xylene solution containing 6.7 ppm phenol was fed into the reactor at 40° C. and 20 WHSV. Samples of outlet liquids were collected at regular intervals and analyzed for the phenol concentration. Results are plotted in FIG. 4.

Example 31

Adsorption on the 1st Cycle Wet-Toluene-Regenerated Selexsorb CDX at 20 WHSV

The spent adsorbent from Example 30 was regenerated with wet toluene at temperature 120° C. at 5 WHSV. The wet toluene contained ~400 ppm $H_2O$ under a continuous N2 flow. Samples of outlet liquids were collected at regular intervals and analyzed for the phenol concentration. The last 46 hours of the regeneration was at 150° C.

Figure 4:
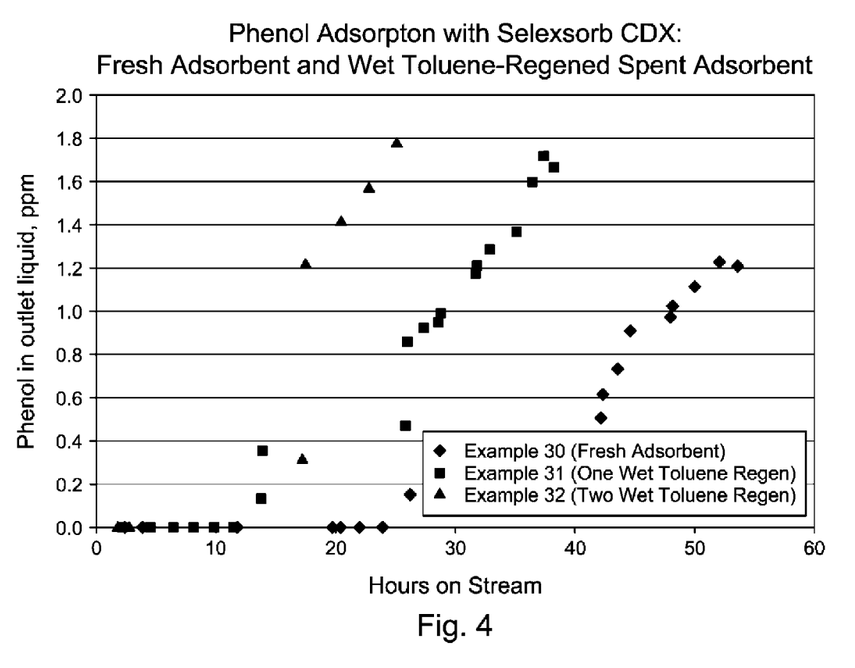

After the wet toluene regeneration, the spent adsorbent was dried at 150° C., then 220° C., and 280° C. for 24 hours, respectively. The dried adsorbent was then used in phenol adsorption, following the same procedure as that of Example 30. Results are shown in FIG. 4.

Example 32

Adsorption on the 2nd Cycle Wet-Toluene-Regenerated Selexsorb CDX at 20 WHSV

The spent adsorbent from Example 31 was regenerated the second time with wet toluene at temperature 150° C. at 5 WHSV, following the same procedure as that of Example 5. The last 46 hours of the regeneration was at 200° C. The regenerated spent adsorbent, after drying at 150° C., then 220° C., and 280° C. for 24 hours, respectively, was used in phenol adsorption, also following the same procedure as that of Example 30. Results are shown in FIG. 4.

The alkylation process employed herein can employ any aromatic feedstock comprising toluene and/or benzene, although in general, it is preferred that the aromatic feed contains at least 90 wt %, especially at least 99 wt % of benzene, toluene or a mixture thereof. An aromatic feed containing at least 99 wt % toluene is particularly desirable. Similarly, although the composition of the methanol- and/or dimethylether-containing feed is not critical, it is generally desirable to employ feeds containing at least 90 wt %, especially at least 99 wt %, of methanol and/or dimethylether. Water is also advantageously used in the feed to the alkylation reaction.

In embodiments said process stream may be subjected to additional process steps such as fractionation, adsorptive separations, crystallization, membrane separation, and the like, to remove species other than phenol.

Figure 1:
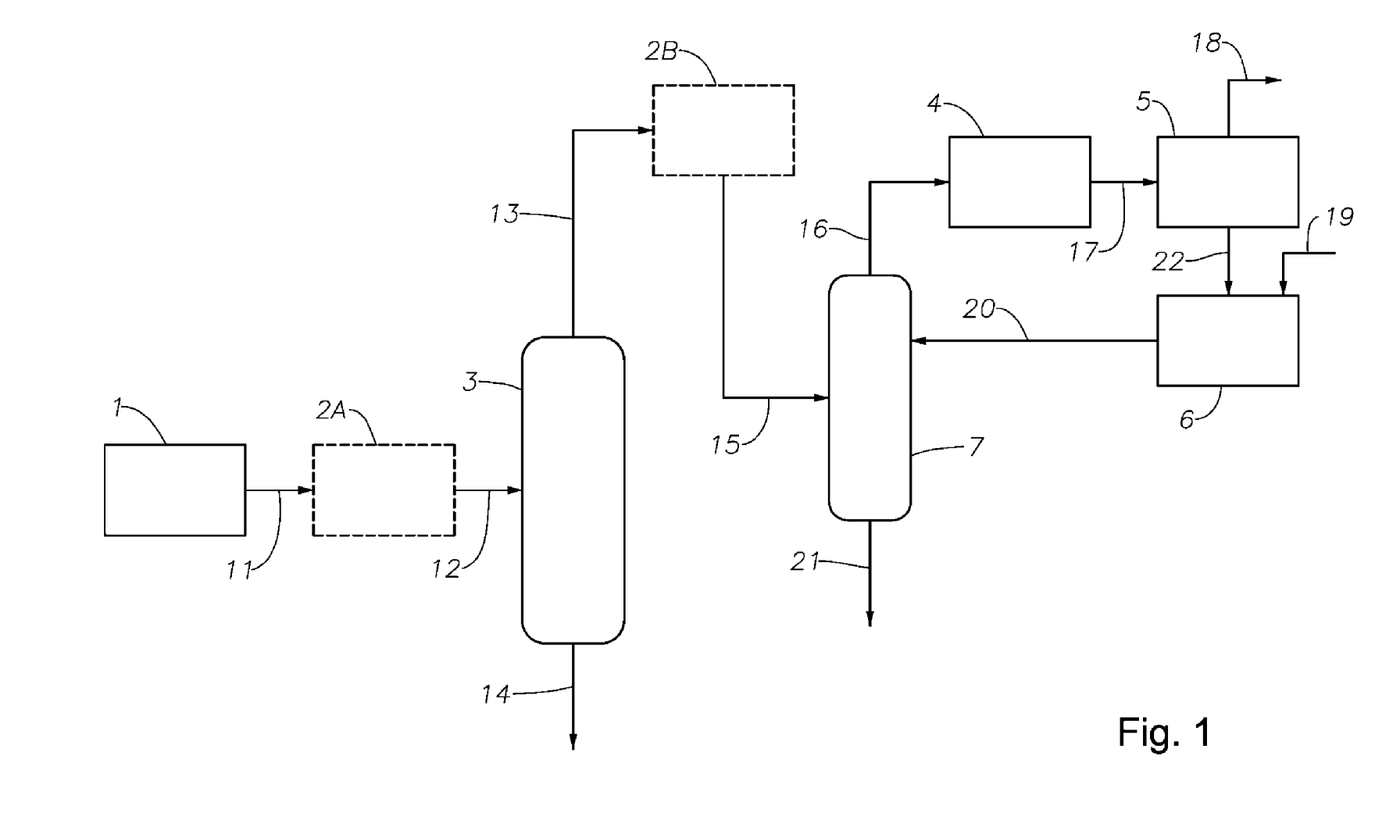
FIGS. 1 and 2 are schematic diagrams showing certain preferred embodiments of the present invention.
Figure 2:
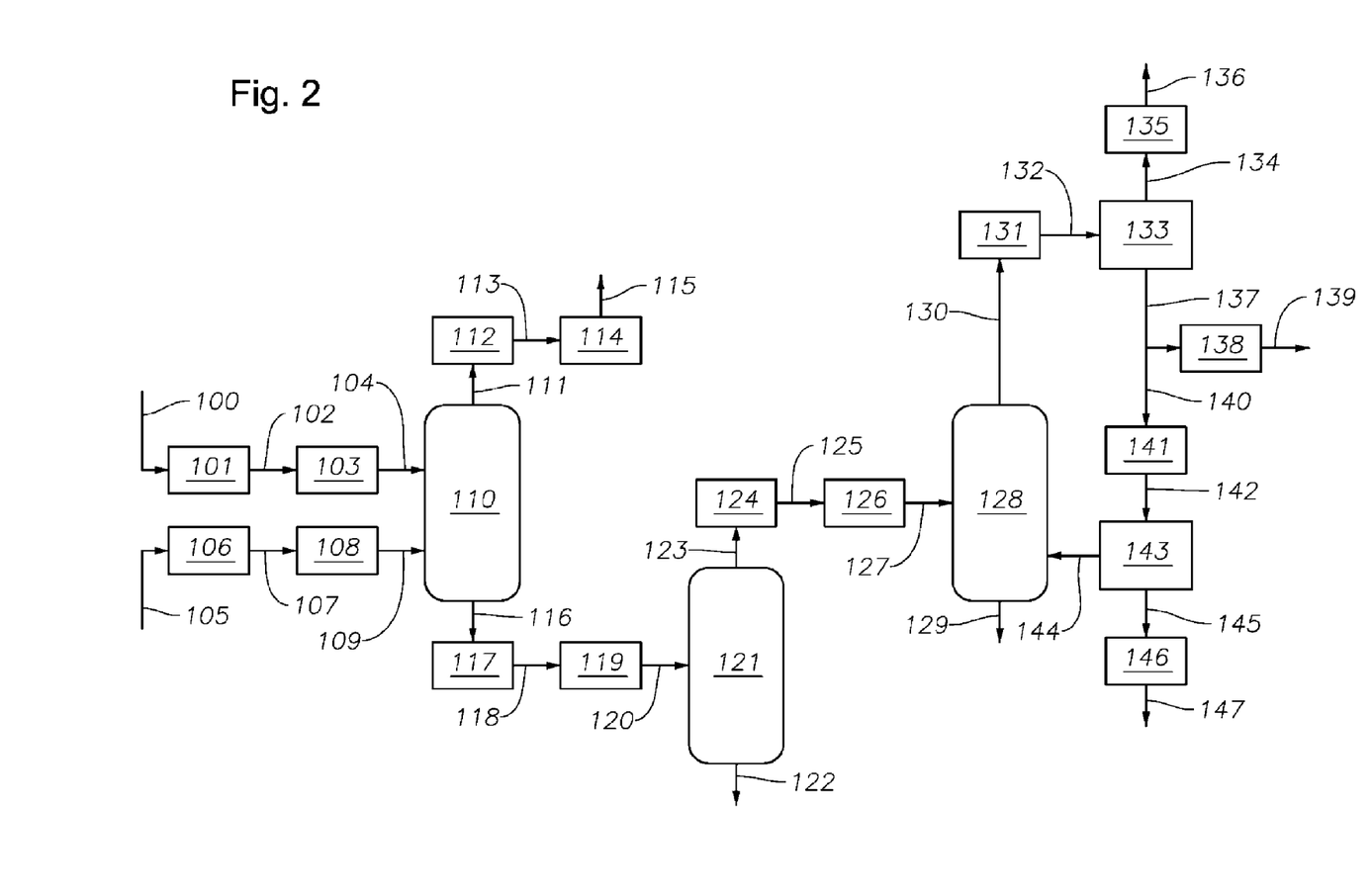

The invention may yet still be even better understood by reference to FIGS. 1 and 2, which are schematic illustrations of preferred embodiments of the invention. One of skill in the art in possession of the present discourse will understand that the invention may be practiced other than as specifically illustrated herein, and the illustrations is not intended to be limiting.

In FIG. 1, apparatus 1 is a reactor suitable for carrying out alkylation of benzene and/or toluene in the presence of a solid acid catalyst, such as ZSM-5, particularly a phosphorus-containing ZSM-5, and more particularly a phosphorus-containing ZSM-5 that has been steamed at temperatures on the order of 1000° F. The specifics of the apparatus 1 do not form a part of the present invention, except as otherwise stated herein, but rather have been described in numerous prior art patents, patent applications, and publications.

The effluent from 1, which is an aromatic hydrocarbon stream rich in paraxylene, such as 70 wt % or more, as described in more detail herein, is passed via conduit 11 to phenol removal unit 2A. The unit 2A is illustrated with dotted lines since it is but one possible placement of such a unit, albeit preferred, according to embodiments of the invention. The phenol-depleted stream rich in paraxylene is passed via conduit 12 to a fractionation column or splitter 3 wherein the stream is split into a paraxylene-enriched overhead passed downstream in the process through conduit 13 and a paraxylene depleted bottoms product passed downstream in the process through conduit 14.

Phenol removal unit 2B illustrates a second possible placement of a phenol removal unit according to the present invention. One or both of 2A and 2B may be used in an embodiment of the process according to the invention. Phenol removal units may comprise one or more vessels containing, by way of example, a fixed bed apparatus comprising the adsorbent. Such units are per se known in the art.

The paraxylene-enriched overhead from splitter 3, is passed via conduit 15 to an optional second fractionation column 7, or in the case where unit 2A is not present, a first phenol removal unit 2B. The paraxylene-enriched stream 15, now having been treated by one or both of phenol removal units 2A and/or 2B is then passed via conduit 15 to fractionator 7 to remove heavies such as aromatic C9+s 21 and pass an overhead 16, comprising an paraxylene-enriched, phenol-depleted stream (relative to effluent 11), further downstream in the process. This stream 16 may optionally be treated in apparatus 4 to remove other impurities, such as other oxygenates, e.g., by caustic wash (see U.S. patent application Ser. No. 13/487,651) or styrene, as explained in U.S. Provisional Patent Application No. 61/653,688. The stream 17 is then sent to paraxylene removal unit 5 of the type known in the art, such as an adsorptive separation unit (e.g., Parex™ unit or Eluxyl™ unit) or separation by crystallization. The final desired high purity paraxylene stream is taken off via conduit 18 and the paraxylene-depleted stream 22, otherwise known as raffinate with respect to paraxylene removal units, is sent to a liquid phase isomerization unit 6, of the type per se well-known in the art, wherein the paraxylene-depleted raffinate is isomerized to equilibrium concentration xylenes (i.e., about 22-24 wt % paraxylene). The isomerization may be liquid phase or vapor phase, each per se known in the art. After isomerization the equilibrium xylenes stream may be recycled via line 20 to fractionator 7 or otherwise processed as desired.

The invention may be still be even better understood by reference to FIG. 2, which is a schematic illustration of another preferred embodiment of the invention. FIG. 2 illustrates apparatus downstream of the alkylation reactor, not shown for convenience of view. In FIG. 2, fresh feed 100, comprising alkylating agents selected from methanol, DME, or a combination thereof, and/or the aromatic species to be alkylated, selected from benzene, toluene, and mixtures thereof, are passed through phenol-removal unit 101 and then via conduit 102 to styrene-removal unit 103, and then through conduit 104 to fractionator 110, which removes toluene overhead to be sent to the alkylation reactor, as described further hereinbelow. One of the advantages of the present invention is that one or more of extracted toluene and non-extracted toluene may be used, and since numerous sources of toluene can be used in the alkylation reactor using a solid acid catalyst, as well as numerous sources of methanol and/or DME alkylating agent. Thus, it is advantageous to have a pre-treatment of the feed(s) in one or both of units 101 and 103 as set forth in FIG. 2, however, use of such pretreatment is optional. It will also be appreciated that the alkylating agent(s) and benzene and/or toluene can be fed separately together, and likewise the choice of whether to have a pre-treatment by one or both of units 101 and 103, in either order, can be made independently on each separate feedstream. Water is advantageously also added to the upstream alkylation reactor and may be added into the system represented by the entirety of the alkylation reactor (not shown) and the apparatus shown in FIG. 2 along with feed 100, or it may be added separately to said system directly to the alkylation reactor; the addition of water and the location of addition is optional. Advantageously, the addition of water into the alkylation reactor is in an amount sufficient to reduce coking of the catalyst. One or more of the feeds may be added preheated and the feed(s) may be added as liquid or vapor to reactor 100.

Continuing with FIG. 2, 105 represents one or more of the recycled reactor products, advantageously previously treated to remove gaseous products (e.g., light olefins) and possibly dried of water, although, as mentioned above, water may be added as part of the feed. The removal of gaseous products and/or water is not shown in FIG. 2 as it does not form a part of the present invention per se, and could be accomplished by one of ordinary skill in the art in possession of the present disclosure. Typically unreacted methanol and/or DME and unreacted benzene and/or toluene are recycled via line 105 or they may be recycled separately, or a combination thereof, and thus pretreatment by phenol-removal unit 106 and/or styrene removal unit 108, fluidly connected to 106 via line 107 and to reactor 110 via line 109, is advantageous.

Continuing with FIG. 2, fractionator tower 110 (or "detol tower") removes toluene overhead and the toluene can optionally be sent via conduit 111 through one or more of phenol removal unit 112 and styrene removal unit 114, fluidly connected by conduit 113, prior to being recycled to the alkylation reactor (again, not shown) via conduit 115. It will be appreciated that the toluene stream 111 may be optionally cooled to a liquid by known methods, not shown, prior to treatment in units 112 and/or 114, and that whether or not to have a phenol removal step and/or styrene removal step between the detol tower 110 and the alkylation reactor, and the order thereof, can be determined independently by one of ordinary skill in the art in possession of the present disclosure.

The bottoms product of detol tower 110, comprising the desired paraxylene-enriched alkylation reactor products, leaves 110 through conduit 116 and may optionally be treated by one or more of the phenol removal unit 117 and/or the styrene removal unit 119, fluidly connected by conduit 118, and is then passed to xylene splitter 121 via conduit 120 to remove heavier products (i.e., C9+ aromatic hydrocarbons) as a bottoms product through conduit 122. The C9+s may be advantageous used with a transalkylation unit integrated with the system shown in FIG. 2, and indeed the entire apparatus shown in FIG. 2, and the alkylation reactor not shown, may be advantageous integrated with other known methods of generating xylenes and/or other aromatic products, for greater efficiency of feedstream use, integration of heat (which in embodiments is generated by the alkylation reactor), and so on.

The overheads 123 from xylene splitter 121 may also optionally be treated by one or both of phenol removal unit 124 and styrene removal unit 126, fluidly connected via conduit 125 prior to being sent via conduit 127 to an optional second xylene splitter 128, which analogous to splitter 121, separates the desired paraxylene-enriched xylenes stream overhead, to conduit 130, from bottoms product 129, which may again be disposed of in the same manner as bottoms product 122.

The overheads 130 may be treated by one or both of a phenol removal unit or styrene removal unit, and in the embodiment of FIG. 2, is illustrated by a single unit 131, which may represent one or more of such units.

The remaining portions of FIG. 2 are similar to the per se well-known xylenes loop, but integrated with the phenol removal step(s) according to the present invention, and thus, the paraxylene-enriched stream 132 is passed to a paraxylene recovery unit 133, which may be an adsorption unit (e.g., Parex adsorption unit or Eluxyl adsorption unit), or a crystallizer unit, or membrane unit, and the like, wherein paraxylene is separated from its C8 aromatic isomers, to yield very high purity paraxylene via conduit 134, which may yet further be treated by one or more of a phenol-removal unit and/or styrene removal unit, represented by a single apparatus 135, to yield a highly pure, highly enriched paraxylene product, having, in embodiments, a paraxylene content of greater than 99.0 wt % (based on the entire content of the stream), and further characterized by a phenol content of less than 10 ppm wt, preferably less than 1.0 ppm wt.

Finally, continuing with the description of the embodiment shown in FIG. 2, the raffinate (paraxylene-depleted xylenes stream) from the paraxylene removal unit 133, leaving via conduit 137, may be recovered as mixed xylenes 139, optionally but advantageously treated by one or more of a styrene removal unit and/or a phenol removal unit, again represented by a single apparatus 138, and/or via conduit 140 to the isomerization unit represented by apparatus 143, optionally but advantageously treated by one or more of a styrene removal unit and/or a phenol removal unit, again represented by a single apparatus 141 which is fluidly connected to isomerization unit 143 by conduit 142. The product of the isomerization unit, as is well-known, will be an equilibrium stream of xylenes, which may be advantageously then recycled back xylenes splitter 128 and/or sent to ethylbenzene purge (not shown) via conduit 145, optionally treated by one or more of phenol removal and/or styrene removal unit, again represented by a single unit 146, leaving said unit, if present, via conduit 147.

The isomerization unit 143 may be liquid phase or gas phase or both may be used in series or parallel. Both liquid and gas phase isomerization processes and units to use in said processes are per se well-known in the art.

The catalyst employed in the alkylation process is generally a porous crystalline material and, in one preferred embodiment, is a porous crystalline material having a Diffusion Parameter for 2,2 dimethylbutane of about 0.1-15 sec$^{-1}$ when measured at a temperature of 120° C. and a 2,2 dimethylbutane pressure of 60 torr (8 kPa).

As used herein, the Diffusion Parameter of a particular porous crystalline material is defined as $D/r^2 \times 10^6$, wherein D is the diffusion coefficient (cm$^2$/sec) and r is the crystal radius (cm). The diffusion parameter can be derived from sorption measurements provided the assumption is made that the plane sheet model describes the diffusion process. Thus, for a given sorbate loading Q, the value $Q/Q_{eq}$, where $Q_{eq}$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

The porous crystalline material is preferably a medium-pore size aluminosilicate zeolite. Medium pore zeolites are generally defined as those having a pore size of about 5 to about 7 Angstroms, such that the zeolite freely sorbs molecules such as n-hexane, 3-methylpentane, benzene and p-xylene. Another common definition for medium pore zeolites involves the Constraint Index test which is described in U.S. Pat. No. 4,016,218, which is incorporated herein by reference. In this case, medium pore zeolites have a Constraint Index of about 1-12, as measured on the zeolite alone without the introduction of oxide modifiers and prior to any steaming to adjust the diffusivity of the catalyst. In addition to the medium-pore size aluminosilicate zeolites, other medium pore acidic metallosilicates, such as silicoaluminophosphates (SAPOs), can be used in the present process.

Particular examples of suitable medium pore zeolites include ZSM-5, ZSM-11, ZSM-12, ZSM-22, ZSM-23, ZSM-35, and ZSM-48, with ZSM-5 and ZSM-11 being particularly preferred. In one embodiment, the zeolite employed in the process of the invention is ZSM-5 having a silica to alumina molar ratio of at least 250, as measured prior to any treatment of the zeolite to adjust its diffusivity.

Zeolite ZSM-5 and the conventional preparation thereof are described in U.S. Pat. No. 3,702,886. Zeolite ZSM-11 and the conventional preparation thereof are described in U.S. Pat. No. 3,709,979. Zeolite ZSM-12 and the conventional preparation thereof are described in U.S. Pat. No. 3,832,449. Zeolite ZSM-23 and the conventional preparation thereof are described in U.S. Pat. No. 4,076,842. Zeolite ZSM-35 and the conventional preparation thereof are described in U.S. Pat. No. 4,016,245. ZSM-48 and the conventional preparation thereof is taught by U.S. Pat. No. 4,375,573. The entire disclosures of these U.S. patents are incorporated herein by reference.

The medium pore zeolites described above are preferred for the present process since the size and shape of their pores favor the production of p-xylene over the other xylene isomers. However, conventional forms of these zeolites have Diffusion Parameter values in excess of the 0.1-15 sec$^{-1}$ range desired for the present process. Nevertheless, the required diffusivity can be achieved by severely steaming the zeolite so as to effect a controlled reduction in the micropore volume of the catalyst to not less than 50%, and preferably 50-90%, of that of the unsteamed catalyst. Reduction in micropore volume is monitored by measuring the n-hexane adsorption capacity of the zeolite, before and after steaming, at 90° C. and 75 torr n-hexane pressure.

Steaming to achieve the desired reduction in the micropore volume of the porous crystalline material can be effected by heating the material in the presence of steam at a temperature of at least about 950° C., preferably about 950 to about 1075° C., and most preferably about 1000 to about 1050° C. for about 10 minutes to about 10 hours, preferably from 30 minutes to 5 hours.

To effect the desired controlled reduction in diffusivity and micropore volume, it may be desirable to combine the porous crystalline material, prior to steaming, with at least one oxide modifier, preferably selected from oxides of the elements of Groups IIA, IIIA, IIIB, IVA, VA, VB and VIA of the Periodic Table (IUPAC version). Conveniently, said at least one oxide modifier is selected from oxides of boron, magnesium, calcium, lanthanum and preferably phosphorus. In some cases, it may be desirable to combine the porous crystalline material with more than one oxide modifier, for example a combination of phosphorus with calcium and/or magnesium, since in this way it may be possible to reduce the steaming severity needed to achieve a target diffusivity value. The total amount of oxide modifier present in the catalyst, as measured on an elemental basis, may be between about 0.05 and about 20 wt %, such as between about 0.1 and about 10 wt %, based on the weight of the final catalyst.

Where the modifier includes phosphorus, incorporation of the modifier in the alkylation catalyst is conveniently achieved by the methods described in U.S. Pat. Nos. 4,356,338; 5,110,776; 5,231,064; and 5,348,643; the entire disclosures of which are incorporated herein by reference. Treatment with phosphorus-containing compounds can readily be accomplished by contacting the porous crystalline material, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 and about 30 wt %.

Representative phosphorus-containing compounds which may be used to incorporate a phosphorus oxide modifier into the catalyst of the invention are set forth in U.S. Pat. No. 6,504,072.

Particular phosphorus-containing compounds include ammonium phosphate, ammonium dihydrogen phosphate, diammonium hydrogen phosphate, diphenyl phosphine chloride, trimethylphosphite, phosphorus trichloride, phosphoric acid, phenyl phosphine oxychloride, trimethylphosphate, diphenyl phosphinous acid, diphenyl phosphinic acid, diethylchlorothiophosphate, methyl acid phosphate, and other alcohol-$P_2O_5$ reaction products.

Representative boron-containing compounds which may be used to incorporate a boron oxide modifier into the catalyst of the invention include boric acid, trimethylborate, boron oxide, boron sulfide, boron hydride, butylboron dimethoxide, butylboric acid, dimethylboric anhydride, hexamethylborazine, phenyl boric acid, triethylborane, diborane and triphenyl boron.

Representative magnesium-containing compounds include magnesium acetate, magnesium nitrate, magnesium benzoate, magnesium propionate, magnesium 2-ethylhexoate, magnesium carbonate, magnesium formate, magnesium oxylate, magnesium bromide, magnesium hydride, magnesium lactate, magnesium laurate, magnesium oleate, magnesium palmitate, magnesium salicylate, magnesium stearate and magnesium sulfide.

Representative calcium-containing compounds include calcium acetate, calcium acetylacetonate, calcium carbonate, calcium chloride, calcium methoxide, calcium naphthenate, calcium nitrate, calcium phosphate, calcium stearate and calcium sulfate.

Representative lanthanum-containing compounds include lanthanum acetate, lanthanum acetylacetonate, lanthanum carbonate, lanthanum chloride, lanthanum hydroxide, lanthanum nitrate, lanthanum phosphate and lanthanum sulfate.

The porous crystalline material employed in the process of the invention may be combined with a variety of binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays, which can be composited with the porous crystalline material, include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the porous crystalline material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of porous crystalline material and inorganic oxide matrix vary widely, with the content of the former ranging from about 1 to about 90% by weight and more usually, particularly when the composite is prepared in the form of beads, in the range of about 2 to about 80 wt % of the composite.

The alkylation process can be conducted in any known reaction vessel but generally the methanol and aromatic feeds are contacted with the catalyst described above with the catalyst particles being disposed in one or more fluidized beds. Each of the methanol and aromatic feeds can be injected into the fluidized catalyst in a single stage. However, in one embodiment, the methanol feed is injected in stages into the fluidized catalyst at one or more locations downstream from the location of the injection of the aromatic reactant into the fluidized catalyst. For example, the aromatic feed can be injected into a lower portion of a single vertical fluidized bed of catalyst, with the methanol being injected into the bed at a plurality of vertically spaced intermediate portions of the bed and the product being removed from the top of the bed. Alternatively, the catalyst can be disposed in a plurality of vertically spaced catalyst beds, with the aromatic feed being injected into a lower portion of the first fluidized bed and part of the methanol being injected into an intermediate portion of the first bed and part of the methanol being injected into or between adjacent downstream catalyst beds.

The conditions employed in the alkylation stage of the present process are not narrowly constrained but, in the case of the methylation of toluene, generally include the following ranges: (a) temperature between about 500 and about 700° C., such as between about 500 and about 600° C.; (b) pressure of between about 1 atmosphere and about 1000 psig (between about 100 and about 7000 kPa), such as between about 10 psig and about 200 psig (between about 170 and about 1480 kPa); (c) moles toluene/moles methanol (in the reactor charge) of at least about 0.2, such as from about 0.2 to about 20; and (d) a weight hourly space velocity ("WHSV") for total hydrocarbon feed to the reactor(s) of about 0.2 to about 1000, such as about 0.5 to about 500 for the aromatic reactant, and about 0.01 to about 100 for the combined methanol reagent stage flows, based on total catalyst in the reactor(s).

The product of the reaction between the methanol and the aromatic feed is a gaseous effluent comprising para-xylene and other xylene isomers, water vapor, unreacted toluene and/or benzene, unreacted methanol, phenolic impurities, light olefins and other light gas by-products, and generally some $C_9+$ aromatic by-products. In addition, where the process is conducted in a fluidized catalyst bed, the effluent will contain some entrained solid catalyst and catalyst fines. Thus, the gaseous effluent leaving the (final) fluidized bed reactor is generally passed through an integral cyclone separator to remove some of the entrained catalyst solids and return them to the alkylation reactor.

The product effluent leaves the alkylation reactor system at a high temperature, typically between about 500 and about 600° C. and initially may be passed through a heat exchanger so that the waste heat in the effluent stream may be recovered and used to heat other process stream(s). It is, however, preferred that any initial cooling of the product stream is limited so as to keep the effluent vapors well above the dew point, typically about 240° F. (116° C.).

Following further cooling, the effluent vapor stream is fed to a separation system, which may comprise one or more fractionation columns, where the unreacted methanol and aromatics are recovered and recycled to the alkylation step, the light and heavy hydrocarbons are removed and the remainder of effluent is separated into a liquid organic phase rich in xylene and a waste water stream. Part of the phenolic impurities is concentrated in the xylene-rich organic phase and part is dissolved in the waste water stream making the waste water stream acidic.

Typically, the phenolic impurities include phenol, methyl phenols and dimethyl phenols and are present in the xylene filtrate in an amount from about 0.2 ppmw to about 1000 ppmw of phenol, from about 0.2 ppmw to about 1000 ppmw of methyl phenols and from about 0.5 ppmw to about 1000 ppmw of dimethyl phenols.

The present invention can be integrated with other systems using toluene and benzene streams, such as selective disproportionation of toluene and/or transalkylation of toluene and aromatic C9+ species.

The invention has been described above with reference to numerous embodiments and specific examples. Many variations will suggest themselves to those skilled in this art in light of the above detailed description.

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

What is claimed is:

1. A process for the production of paraxylene comprising:
    (a) reacting toluene and/or benzene with an alkylating agent selected from methanol, dimethylether (DME), and mixtures thereof, in the presence of a catalyst comprising a porous crystalline material having a Diffusion Parameter for 2,2 dimethylbutane of about 0.1-15 $sec^{-1}$ when measured at a temperature of 120° C. and a 2,2 dimethylbutane pressure of 60 torr (8 kPa), wherein said porous crystalline material has undergone prior treatment with steam at a temperature of at least 950° C. for between about 10 minutes and about 100 hours to adjust the Diffusion Parameter of said material to about 0.1-15 $sec^{-1}$, under appropriate conditions to produce an aromatic hydrocarbon stream comprising paraxylene and phenolic impurities; and
    (b) contacting said aromatic hydrocarbon stream with a suitable adsorbent to remove the phenolic impurities selectively, so as to provide a product stream having lower concentration of phenolic impurities than said aromatic hydrocarbon stream, wherein the amount of phenolic impurities removed from said aromatic hydrocarbon stream is greater than the amount of benzene produced or paraxylene isomerized by said contact, and wherein said adsorbent is selected from alumina, silica, molecular sieves, basic organic resins, and mixtures thereof.

2. The process according to claim 1, wherein said product stream comprises less than 10 ppm wt of phenolic impurities.

3. The process according to claim 1, wherein said product stream comprises less than 1.0 ppm wt of phenolic impurities.

4. The process according to claim 1, wherein the phenolic impurities include phenol, methyl phenols and dimethyl phenols.

5. The process of claim 1, wherein said Diffusion Parameter of said porous crystalline material is about 0.5-10 $sec^{-1}$.

6. The process of claim 1, wherein said porous crystalline material has undergone prior treatment with steam at a temperature of at least 1000° C. for between about 10 minutes and about 100 hours.

7. The process of claim 6, wherein said treatment with steam reduces the pore volume of the catalyst to not less than 50% of that of the pore volume of the catalyst before said treatment with steam.

8. The process of claim 1, wherein the catalyst contains at least one oxide modifier selected from the group consisting of oxides of elements of Groups IIA, IIIA, IIIB, IVA, IVB, VA and VIA of the Periodic Table.

9. The process of claim 1, wherein the catalyst contains at least one oxide modifier selected from the group consisting of oxides of boron, magnesium, calcium, lanthanum and phosphorus.

10. The process of claim 9, wherein the catalyst contains about 0.1 to about 10 wt % of the oxide modifier based on the elemental modifier.

11. The process of claim 1, wherein the catalyst has an average particle size of about 20 to 200 microns.

12. The process of claim 1, wherein the catalyst comprises a phosphorus-containing ZSM-5 catalyst.

13. The process according to claim 1, wherein said aromatic hydrocarbon stream further comprises styrene and said process includes removing at least a portion of said styrene.

14. The process according to claim 1, further comprising:
(c) recovering the paraxylene via adsorptive separation or crystallization to produce a paraxylene-enriched stream and a paraxylene-depleted stream.

15. The process according to claim 14, further comprising:
(d) isomerizing the paraxylene-depleted stream in the vapor phase, liquid phase, or a combination thereof in series or parallel, to produce equilibrium xylenes.

16. The process according to claim 1, further including a step of regenerating said adsorbent.

17. The process according to claim 16, wherein said step of regenerating said adsorbent is selected from at least one of: (1) purge with mixture(s) of at least one inert gas and at least one organic solvent selected from aromatics, alcohols, ketones, water, $CO_2$, $CS_2$, and mixtures thereof, at a temperature >20° C.; (3) purge with an organic solvent selected from at least one of aromatics, alcohols, ketones, water, $CO_2$, $CS_2$, and mixtures thereof at a temperature >20° C., followed by an inert gas purge at a temperatures >100° C.; (4) purge with mixture(s) of at least one organic solvent and at least one inorganic solvent at a temperature >25° C., followed by an inert gas purge at a temperature >150° C.; and (5) purge with air, mixture of oxygen and nitrogen, steam, or mixture thereof at a temperature >150° C.

\* \* \* \* \*